United States Patent
Wolfe et al.

(10) Patent No.: US 11,143,582 B2
(45) Date of Patent: Oct. 12, 2021

(54) SENSOR SYSTEM FOR DETECTING CONTAMINANT IN FLUID

(71) Applicant: Parker-Hannifin Corporation, Cleveland, OH (US)

(72) Inventors: Lewis A. Wolfe, Colorado Springs, CO (US); Jeffery W. Gibson, Colorado Springs, CO (US); Thomas Muzik, Colorado Springs, CO (US); Michael A. White, Amherst, MA (US)

(73) Assignee: Parker-Hannifin Corporation, Cleveland, OH (US)

( * ) Notice: Subject to any disclaimer, the term of this patent is extended or adjusted under 35 U.S.C. 154(b) by 0 days.

(21) Appl. No.: 16/647,542

(22) PCT Filed: Sep. 21, 2018

(86) PCT No.: PCT/US2018/052152
§ 371 (c)(1),
(2) Date: Mar. 16, 2020

(87) PCT Pub. No.: WO2019/152079
PCT Pub. Date: Aug. 8, 2019

(65) Prior Publication Data
US 2020/0217769 A1 Jul. 9, 2020

Related U.S. Application Data

(60) Provisional application No. 62/624,390, filed on Jan. 31, 2018.

(51) Int. Cl.
*G01N 15/02* (2006.01)
*G01N 15/06* (2006.01)
*G01N 33/22* (2006.01)

(52) U.S. Cl.
CPC .......... *G01N 15/0211* (2013.01); *G01N 15/06* (2013.01); *G01N 33/22* (2013.01); *G01N 2015/0693* (2013.01)

(58) Field of Classification Search
CPC .... G01N 15/06; G01N 33/22; G01N 15/0211; G01N 2015/0011; G01N 2015/0046;
(Continued)

(56) References Cited

U.S. PATENT DOCUMENTS 5,438,420 A 8/1995 Harwick et al.
5,939,727 A 8/1999 Sommer
(Continued)

FOREIGN PATENT DOCUMENTS

GB 2 265 217 9/1993

OTHER PUBLICATIONS

International Search Report and Written Opinion issued by WIPO for corresponding patent application PCT/US2018/052152 dated Jan. 7, 2019.
(Continued)

*Primary Examiner* — Tri T Ton
(74) *Attorney, Agent, or Firm* — Renner, Otto, Boisselle & Sklar, LLP (57) ABSTRACT

A sensor system for sensing contaminants within a fluid stream of a fluid system includes a sensor body and an arm extending from the sensor body to a distal end of the arm, a laser light source configured to direct a laser beam outwardly from an outlet of the sensor body, and a light sensor. A fiber optic light guide is disposed in the sensor body and extends from the light sensor to an inlet of the sensor body for directing light to the light sensor. A beam dump is positioned at the distal end opposite the laser light source to absorb at least a portion of the laser beam directed towards the distal end. A blocking member of the arm is disposed
(Continued)

intermediate between the sensor body and the distal end and is configured to partially restrict a field of intake of light at the inlet.

13 Claims, 4 Drawing Sheets

(58) Field of Classification Search
CPC ... G01N 2015/0053; G01N 2015/0687; G01N 2015/0693; G01N 2021/8528; G01N 21/53; G01N 21/8507; G01N 21/94; G01N 33/2835
USPC .................................................. 356/335–343
See application file for complete search history.

(56) References Cited

U.S. PATENT DOCUMENTS

| | | |
|---|---|---|
| 6,710,878 B1 | 3/2004 | Dean et al. |
| 7,518,719 B2 | 4/2009 | Sprenger et al. |
| 7,948,621 B2 | 5/2011 | Burns et al. |
| 8,498,750 B2 | 7/2013 | Stevens et al. |
| 9,322,682 B2 | 4/2016 | White et al. |
| 2002/0039186 A1 | 4/2002 | Rosenberg |
| 2004/0004717 A1 | 1/2004 | Reed et al. |
| 2015/0020909 A1* | 1/2015 | White .................. G01F 1/0755 138/104 |

OTHER PUBLICATIONS

"Afguard Sensor Technology," Faudi Aviation GmbH, http://www.faudi-aviation.com.

* cited by examiner

SENSOR SYSTEM FOR DETECTING CONTAMINANT IN FLUID

RELATED APPLICATIONS

This application is a national stage application pursuant to 35 U.S.C. § 371 of PCT/US2018/052152 filed Sep. 21, 2018, which claims the benefit of U.S. Provisional Application No. 62/624,390 filed Jan. 31, 2018, the contents of which are incorporated herein by reference.

FIELD OF INVENTION

The present invention relates generally to contaminant monitoring, and more particularly to a sensor system for monitoring a fluid stream to detect a level of contaminant in the fluid stream.

BACKGROUND

Refueling systems are known in the art, by which fuel is transferred from a fuel source to a fuel consuming device, such as a vehicle. In an example of such system, a refueling vehicle provides a source of fuel for refueling a second vehicle. Refueling vehicles, for example, are commonly used for refueling aircraft. The fuel entering the second vehicle is typically monitored for contaminants, such as solid, liquid, and liquid aerosol contaminants. Contaminants can wear components and/or accumulate over time to clog equipment or lower efficiency of fluid systems. Thus, contaminants can have damaging effects on fluid systems, causing critical failures or shortening typical life cycles of components.

In minimizing contaminants within such fuel flow systems, filtration and separation equipment may be implemented. Nonetheless, there remains a need to verify the cleanliness level, or vice versa to assess the contamination level, in fluid flow entering fluid systems or already circulating within fluid systems. Conventional sensor systems for monitoring fluid flow for contaminant level often do not provide adequate results regarding actual contaminant level due to an inability to provide stable results with varying fuel flows, or due to too great of sensitivity to optical changes or measurement shift related to the sensor systems. Furthermore, sizes and configurations of conventional sensor systems for being inserted into fluid streams in fluid systems are too large or wrongly shaped for use with conventional fittings such as standard quarter-inch NPT fittings, that are commonly provided with these fluid systems. As a result, pipe sections often must be specially cut or provided with undesirably large or specially designed fittings to allow for insertion of conventional sensor systems.

SUMMARY OF INVENTION

The present invention provides improved sensor system configurations, particularly for use with fueling or refueling systems, that improve upon one or more of the deficiencies of conventional sensor systems. Sensor systems of the present invention utilize a laser light source for generating a laser beam, and a fiber optic light guide for transmitting light received at an inlet of the sensor system to a light sensor. This combination provides for a stable and less sensitive sensor system with respect to optical changes and measurement shift typically experienced in conventional systems. Furthermore, the sensor systems of the present invention are configured for insertion into a pipe section using a standard quarter-inch NPT fitting. No cutting of pipe sections or specially designed fittings are required.

For example, one sensor system embodiment, for sensing contaminants within a fluid stream of a fluid system, includes a sensor body and an arm extending from the sensor body to a distal end of the arm, a laser light source configured to direct a light beam outwardly from an outlet of the sensor body, and a light sensor. A fiber optic light guide is disposed in the sensor body and extends from the light sensor to an inlet of the sensor body for directing light to the light sensor. A beam dump is positioned at the distal end opposite the light source to absorb at least a portion of the light beam directed towards the distal end. A blocking member of the arm is disposed intermediate the sensor body and the distal end and is configured to partially restrict a field of intake of light at the inlet.

According to one aspect of the invention a sensor system, for sensing contaminants within a fluid stream, includes a sensor body, a laser light source disposed in the body to emit a laser beam and the laser light source is aligned to direct the laser beam outwardly from an outlet of the sensor body, a light sensor disposed in the sensor body, and a light guide disposed in the sensor body and extending from the light sensor to a distal end opposite the light sensor at an inlet of the sensor body. The light guide is aligned for directing light through the sensor body to the light sensor to enable receipt of the light by the light sensor.

The light guide may be a fiber optic light guide.

The inlet of the sensor body may be disposed adjacent the outlet of the sensor body.

The light guide may extend along a guide axis that is transverse to a projection axis of the laser beam extending from the laser light source to the outlet of the sensor body.

The sensor system further may include a processor disposed in the sensor body and configured to convert electrical signals from the light sensor into digital data pertaining to one or both of intensity or consistency of the light received by the light sensor.

The sensor system further may include a processor operatively connected to the light source and to the light sensor for powering the light source and the light sensor, and for calculating contaminant levels in the fluid stream corresponding to properties of the light received by the light sensor.

The sensor system further may include an arm extending from the sensor body, wherein the arm includes a shelf positioned to limit a field of intake of light of the inlet.

The light guide may extend along a guide axis and the shelf is positioned to be intersected by the guide axis.

The shelf may be positioned along the arm between the sensor body and a distal end of the arm opposite the sensor body.

The sensor system further may include an arm extending from the sensor body to a distal end of the arm, wherein a beam dump may be disposed at the distal end of the arm, and wherein the light source may be positioned to direct the laser beam towards the beam dump for absorbing at least a portion of light of the laser beam.

The arm may include a shelf positioned along the arm between the sensor body and the beam dump, and the shelf may be positioned to block at least a portion of light scattered by the beam dump from being received at the inlet.

The sensor system further may include external threads for securing the sensor system within an opening in a fluid system.

The sensor system at the external threads may be sized to be received into a quarter-inch NPT fitting.

According to another aspect of the invention, a sensor system, for sensing contaminants within a fluid stream, includes a sensor body and an arm extending from the sensor body to a distal end of the arm. The sensor system further includes a light source disposed in the sensor body and configured to direct a light beam outwardly from an outlet of the sensor body towards the distal end of the arm. A light sensor is disposed in the sensor body and the sensor body has an inlet disposed opposite the light sensor. The inlet is positioned to receive and direct light towards the light sensor. A beam dump is positioned at the distal end opposite the light source to absorb at least a portion of the light beam directed towards the distal end, thereby preventing the absorbed portion of the light beam from being reflected back towards the inlet. The arm includes a shelf disposed intermediate between the sensor body and the distal end, and the shelf is configured to partially restrict a field of intake of light of the inlet.

The shelf may extend transversely relative to a longitudinal axis of the arm along which the arm extends.

The shelf may be positioned to block at least a portion of light scattered and not absorbed by the beam dump from being received at the inlet.

The arm may include a passage through the arm for allowing flow of the fluid stream therethrough to minimize effect of the arm on the fluid stream.

The sensor body may include external threads for securing the sensor system within an opening in a fluid system, and the sensor system at the external threads may be sized to be received into a quarter-inch NPT fitting.

The sensor system may be in combination with a fluid system having a quarter-inch NPT fitting defining a port for securely receiving the sensor system. The sensor body may have external threads sized to be received into the quarter-inch NPT fitting, and the fitting may have corresponding fitting threads for engaging the external threads.

According to yet another aspect of the invention, a method of sensing contaminants within a fluid stream includes the steps of: (a) emitting a laser beam into the fluid stream that may include a contaminant, (b) receiving at a light guide light from the laser beam reflected from the fluid stream, (c) transmitting the light along the light guide to a light sensor, (d) analyzing one or more properties of the light and (e) determining the level of contaminant in view of the one or more properties.

The method may further include partially absorbing light of the laser beam to prevent the absorbed portion of the laser beam from being reflected back towards the inlet.

The method may further include partially blocking light from being received at the light guide with a blocking member spaced from a distal end of the light guide opposite the light sensor.

The foregoing and other features of the invention are hereinafter described in greater detail with reference to the accompanying drawings.

BRIEF DESCRIPTION OF THE DRAWINGS

The annexed drawings, which are not necessarily to scale, show various aspects of the disclosure.

DETAILED DESCRIPTION

The principles of the present invention have general application to measurement and detection of contaminant accumulation in a fluid, and more particular application to measurement and detection of contaminant, such as water, in fuel being transferred, such as from a refueling container to a vehicle using the fuel to generate power. For example, a sensor system according to the present invention may be used as a final fuel quality sensor before fuel enters a storage vessel of a vehicle, such as an aircraft, ground vehicle, marine vehicle, or the like, such as being inserted at a distal end of a refueling line of a hydrant servicer, hydrant cart, or mobile refueling tanker. It will be appreciated that the principles of the present invention may have application in military or commercial refueling environments, and also may be suitable for measurement and detection of contaminant in hydraulic fluid, oil such as turbine oil, or refrigerant. A fluid analyzed by the sensor system includes a liquid, and may alternatively include a gas, an aerosol, or both. The sensor system may be configured to detect levels of liquid, gas, aerosol, mist or solid contaminant, or a combination of one of more of theses contaminants.

Figure 1:
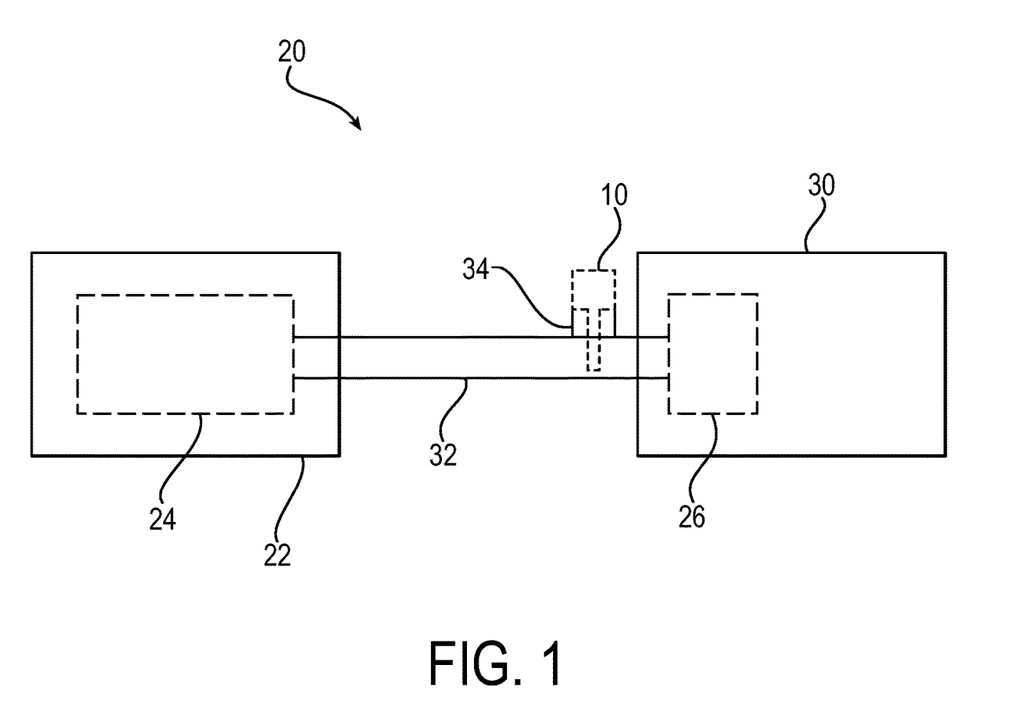
FIG. 1 is schematic view of a fluid system for having a fluid flow through the fluid system for analysis by an exemplary sensor system of the present invention.

Turning first to FIG. 1, a schematic drawing illustrates a typical use of a sensor system 10 according to the present invention, in a fluid system 20. The fluid system 20 includes a first device 22 having a first storage container 24. The first storage container 24 is in fluid communication with a second storage container 26 of a second device 30 by a pipe section 32 defining a passage for allowing transfer of fluid from the first storage container 24 to the second storage container 26.

The sensor system 10 is coupled to the fluid system 20, at the pipe section 32, adjacent the second device 30. A fitting 34, such as a standard NPT fitting, is provided at the passage 32 in which the sensor system 10 is received. This position of the sensor system 10 proximate the second storage container 26 enables the sensor system 10 to provide a final quality check of the fluid before the fluid enters the second storage container 26. The fluid system 20 may include a pump (not shown) at either of the first device 22 or the second device 30 for pumping fluid between the first and second storage containers 24 and 26.

In one embodiment, the first device 22 may be a refueling vehicle and the second device 24 may be a vehicle needing refueling, each having a respective fuel storage tank 24 or 26 for storing fuel. The pipe section 32 may be a section of fuel transfer piping or tubing extended between the first and second storage tanks 24 and 26. The sensor system 10 may be specifically configured to determine a level of contaminant in a specific fuel type being transferred through the pipe section 32. In some embodiments, the fluid system 20 may include a shutoff valve disposed at an end of the pipe section 32, downstream of the sensor system 10. The sensor system 10 may serve as a go-no-go gauge for determining whether the fuel is of a sufficient quality level before entering the storage tank 26. The sensor system 10 may be configured to provide a signal to the shutoff valve or to a control device controlling the shutoff valve to cause closure of the shutoff valve if a threshold level of contaminant is reached in the fuel stream being analyzed by the sensor system 10.

Figure 2:
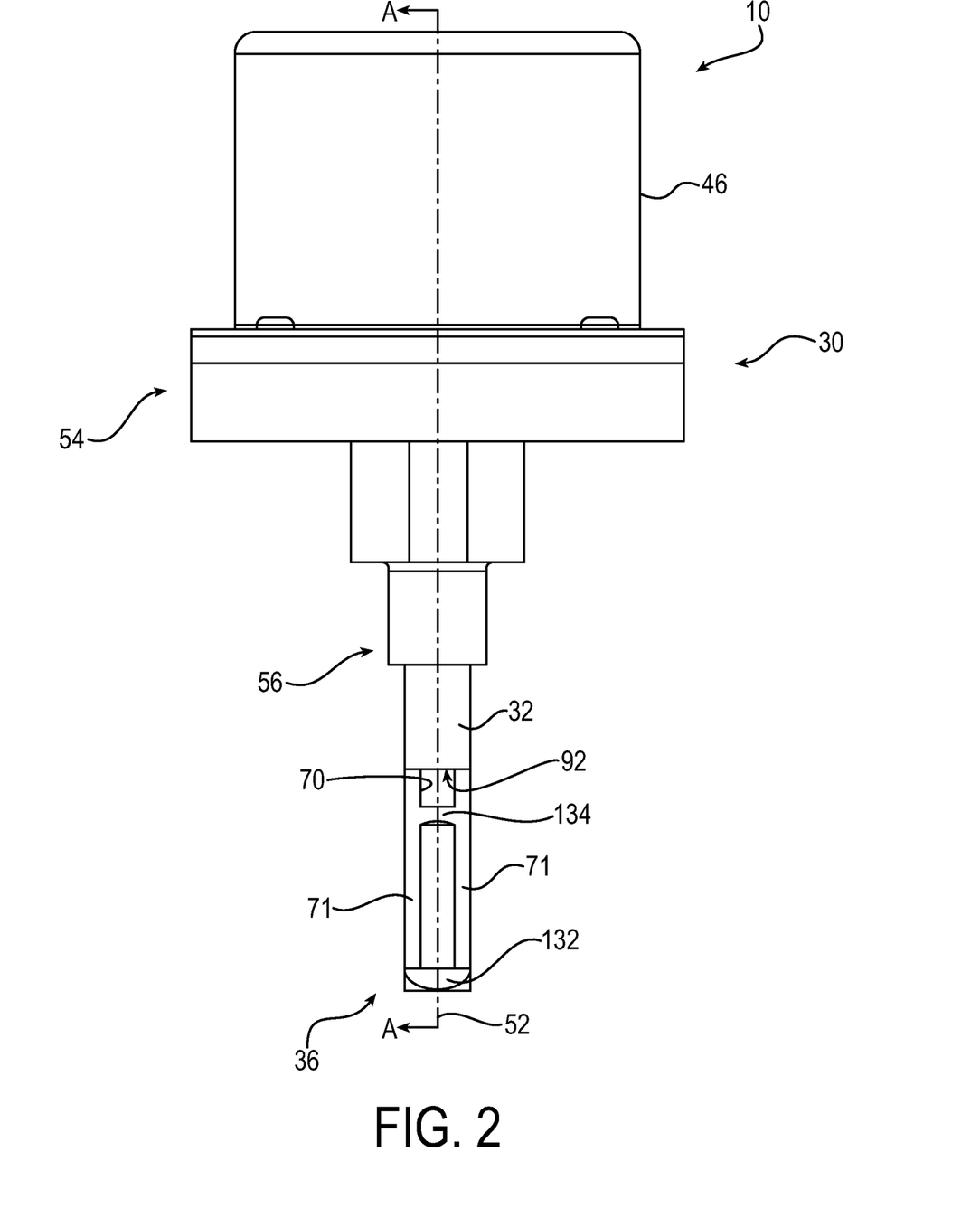
FIG. 2 is an elevational view of the exemplary sensor system of the present invention.
Figure 3:
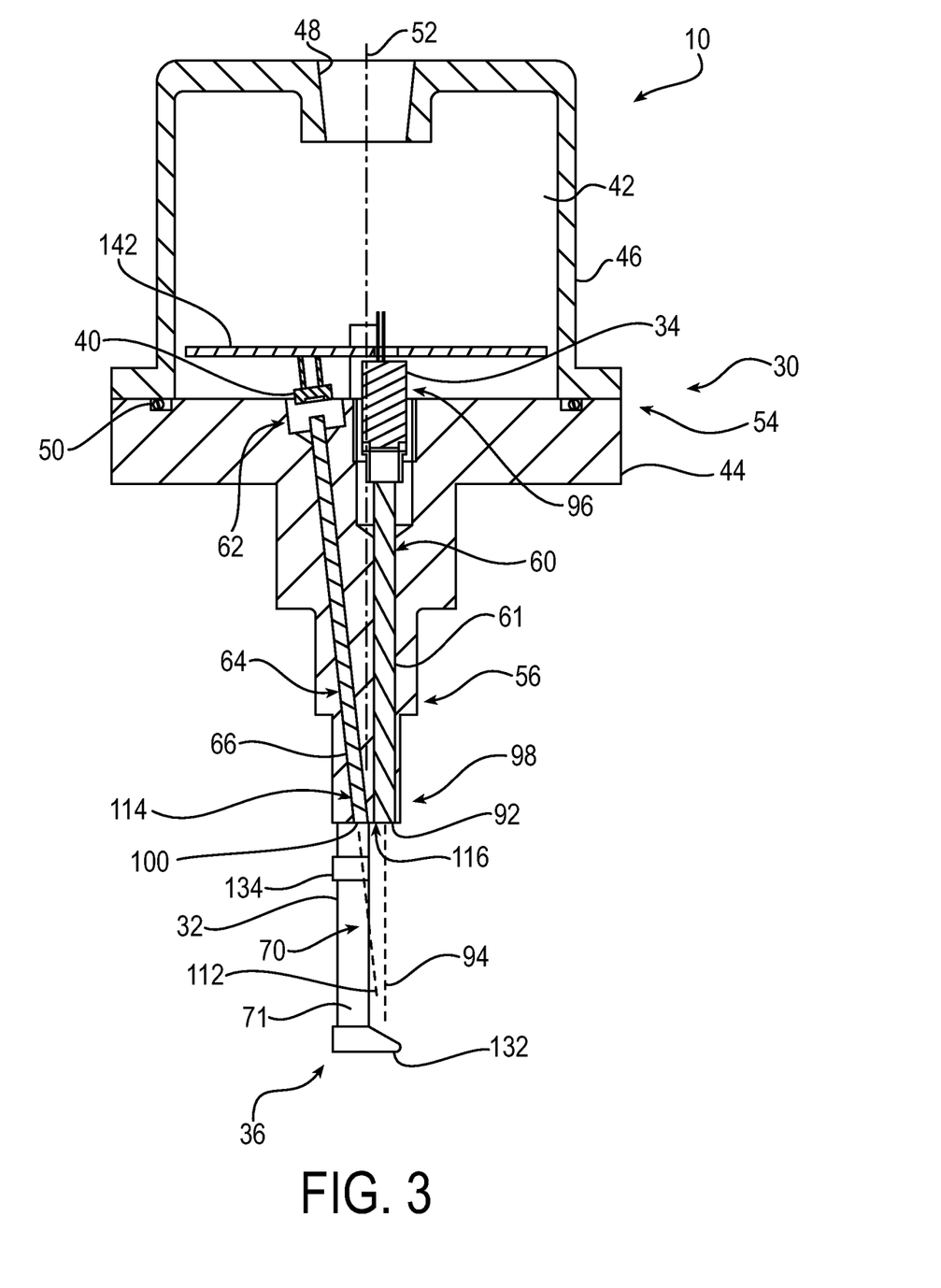
FIG. 3 is a cross-sectional view of the sensor system of FIG. 2, taken along line A-A of FIG. 2.

Referring next to FIGS. 2 and 3, the sensor system 10 is shown in detail, and includes a sensor body 30, an arm 32 extending from the sensor body 30, a light source 34 configured to emit a light beam towards a distal end 36 of the arm 32, and a light sensor 40 configured to receive light for analysis of the light. Generally, the sensor system 10 is configured to be inserted directly into a fluid stream and to emit the light beam into the fluid stream. Light from the light beam that is reflected off contaminant in the fluid is received at the light sensor 40, which is configured to measure one or more properties of the light received, such as intensity, consistency, and quantity of the light.

The sensor body 30 is configured, such as being shaped and having an internal cavity 42, for housing at least a portion of one or both of the light source 34 and the light sensor 40 relative to one another. The internal cavity 42 is defined by a main body portion 44 and a cap portion 46 that is couplable to the main body portion 44, such as via threads. As depicted in FIG. 3, the light sensor 40 and the light source 34 each extends from respective receptacles in the main body portion 40 to the internal cavity 42.

The cap portion 46 includes a passage 48 extending through the cap portion 46 into the internal cavity 48 for allowing access to components within the internal cavity 42, without removal of the cap portion 46 from the main body portion 44. The passage 48 may be sealed by a plug (not shown), which may be coupled to the cap portion 46 by any suitable means such as threads, fasteners, interlocking portions, or comparable. A seal 50, such as an o-ring, provides a seal between the main body portion 44 and the cap portion 46.

The main body portion 44 extends along a body axis 52 between a proximal end 54 adjacent the cap portion 46 and a distal end 56 disposed opposite the proximal end 54. A light source receptacle 60 extends along the body axis 52 between the proximal and distal ends 54 and 56, such as extending fully through the main body portion 44, for receiving the light source 34 and a light source guide 61.

A light sensor receptacle 62 is disposed adjacent the light source receptacle 60 at the proximal end 54 of the main body portion 44. A light guide receptacle 64 extends between the light sensor receptacle 62 and the distal end 56 of the main body portion 44, generally along the body axis 52, though aligned at an angle offset from the body axis 52, for receipt of a light guide 66.

The arm 32 extends from the distal end 56 of the main body portion 44, outwardly from the main body portion 44 and along the body axis 52 to the distal end 36 of the arm 32. The arm 32 generally is cylindrically-shaped and has a minimal cross-sectional profile orthogonal to the body axis 52 to allow for minimal effect on the fluid stream of a fluid system in which the arm 32 is inserted. The arm 32 also defines a passage 70 through the arm 32. The passage 70 extends longitudinally along the body axis 52 and also extends laterally through the arm 32 in a direction orthogonal to the body axis 52. The passage 70 separates the arm into adjacent longitudinally-extending arm portions 71 that each extend along the body axis 52 and define the passage 70 between the arm portions 71. The inclusion of the passage 70 further allows the arm 32 to have a minimized effect on the fluid stream flowing around, past and through the arm 32, such as to provide for minimum drag on the fluid stream.

The sensor body 30 and the arm 32 are made of a material suitable for insertion into a particular fluid stream for which the sensor system 10 is being used to measure contaminant. For example, the sensor body 30 and arm 32 may be made of aluminum or another suitable metal.

The light source 34 received into the light source receptacle 60 of the sensor body 30 is configured to direct a light beam outwardly from an outlet 92 of the sensor body 30 towards the distal end 36 of the arm 32. In the depicted embodiment, the light source 34 is a laser light source that is configured to emit a laser beam. An exemplary laser light source 34, such as for use in detecting water contaminant emulsified in fuel, provides light having a red color. For example, the laser may provide light having a wavelength in the range of about 620 nm to about 750 nm, or about 660 nm to about 710 nm, or about 660 nm. Alternatively, the laser may provide light having an ultraviolet color. Output power of the exemplary laser light source 34 may be in the range of about 10 mw to about 50 mw, or about 15 mw to about 35 mw, or about 20 mw to about 30 mw, or about 25 mw, or about 35 mw.

The light source receptacle 60 receiving the light source 34 is aligned in the main body portion 44 such that a projection axis 94, along which the laser beam is emitted, extends toward and intersects the distal end 36 of the arm 32. The projection axis 94 extends parallel to the body axis 52, allowing for the sensor system 10 to maintain a minimal profile disposed about the beam axis 52 of a portion of the sensor system 10 that is received into the respective fluid system. The projection axis 94 and light source receptacle 60 may be otherwise aligned in other embodiments.

The light source 34 is aligned in the sensor body 30 such that the light source 34 extends between the cavity 42 at a light source proximal end 96 and the light source guide 61. The light source guide 61 extends between the light source 34 and the outlet 92 at a light source guide distal end 98. The light source guide distal end 98 is generally aligned such that the light source guide 61 does not extend beyond or out of the sensor body 30 at the outlet 92, to prevent blocking of light to the light sensor 40 at an inlet 100 of the sensor body 30, which is disposed adjacent the outlet 92.

The depicted light source guide 61, which is shown as a glass rod, is aligned adjacent the light source 34 via its placement in the light source receptacle 60. In some embodiments the light source guide 61 may be coupled to the light source 34, such as being removably coupled. In some embodiments, the light source guide 61 may include a combination of glass and polymer.

The laser light source 34 and light source guide 61 are sealed in the sensor body 30 such as via an adhesive at one or both of the proximal and distal ends 96 and 98. For example, a urethane adhesive may be used.

Turning now to receipt of light at the sensor body 30, light is received at the light sensor 40 by way of the inlet 100 and the light guide 66. The light may be received from the laser beam emitted by the laser light source 34 and reflected from a respective fluid stream, such as off of contaminant in the fluid stream, for example. The light sensor 40 is depicted as being a photodiode, although other light sensors may be suitable. The depicted photodiode light sensor 40 is configured to output electrical signals relating to light received at the photodiode light sensor 40, such as to a processor 110, to be further detailed.

The light received at the light sensor 40 is first received at the inlet 100 of the sensor body 30. The inlet 100 is disposed at the distal end 56 of the main body portion 44, adjacent the outlet 92. Provision of the inlet 100 adjacent the outlet 92 allows a size of the portion of the sensor body 30 received into a respective fluid system to be minimized. The adjacent placement is enabled due to the light sensor 40 receiving light from the laser light beam or light reflected off of the contaminant, instead of the sensor system 10 being configured to direct the laser light beam directly or reflectively towards the inlet 100, and thus requiring a larger sensor system profile.

Furthermore, a single inlet 100 is provided for receiving and directing light towards the light sensor 40, as opposed to multiple inlets 100. The inlet 100 is disposed at the passage 70 through the arm 32, with the projection axis 94 of the laser beam being radially offset from the inlet 100 and from the arm 32, at the location of the inlet 100 and outlet 92. It will be appreciated that two or more inlets may be included in alternative embodiments.

The illustrated light guide 66 extends from the inlet 100 to the light sensor 40. The depicted light guide 66 is a fiber optic light guide 66 including suitable fiber optic cable material, such as having a glass rod core enclosed in a polymer jacket. Some embodiments may include a polymer being used as the optical transmission media or a combination of glass and polymer. In other embodiments, the light guide 66 may not include fiber optic components.

The depicted fiber optic light guide 66 extends along a guide axis 112 that is transverse, i.e., angled relative to, the projection axis 94 of the depicted laser light source 34. The relative angle of the fiber optic light guide 66 in relation to the projection axis 94 allows for light from the laser beam to more easily be received at the inlet 100 at the distal end 114 of the fiber optic light guide 66 and ultimately transmitted to the light sensor 40. At least the distal end 114 of the light guide 66 is secured in the light guide receptacle 64, such as via use of an adhesive, such as urethane adhesive, to aid in securing the distal end 114 relative to an end face 116 of the distal end 56 of the main body portion 44. The distal end 114 of the fiber optic light guide 66 terminates at the end face 116 of the main body portion 44, and does not extend past the distal end 56 or outwardly of the main body portion 44. This alignment aids in preventing light from the laser beam initially emitted at the outlet 92 from being immediately received at the distal end 114.

Figure 4:
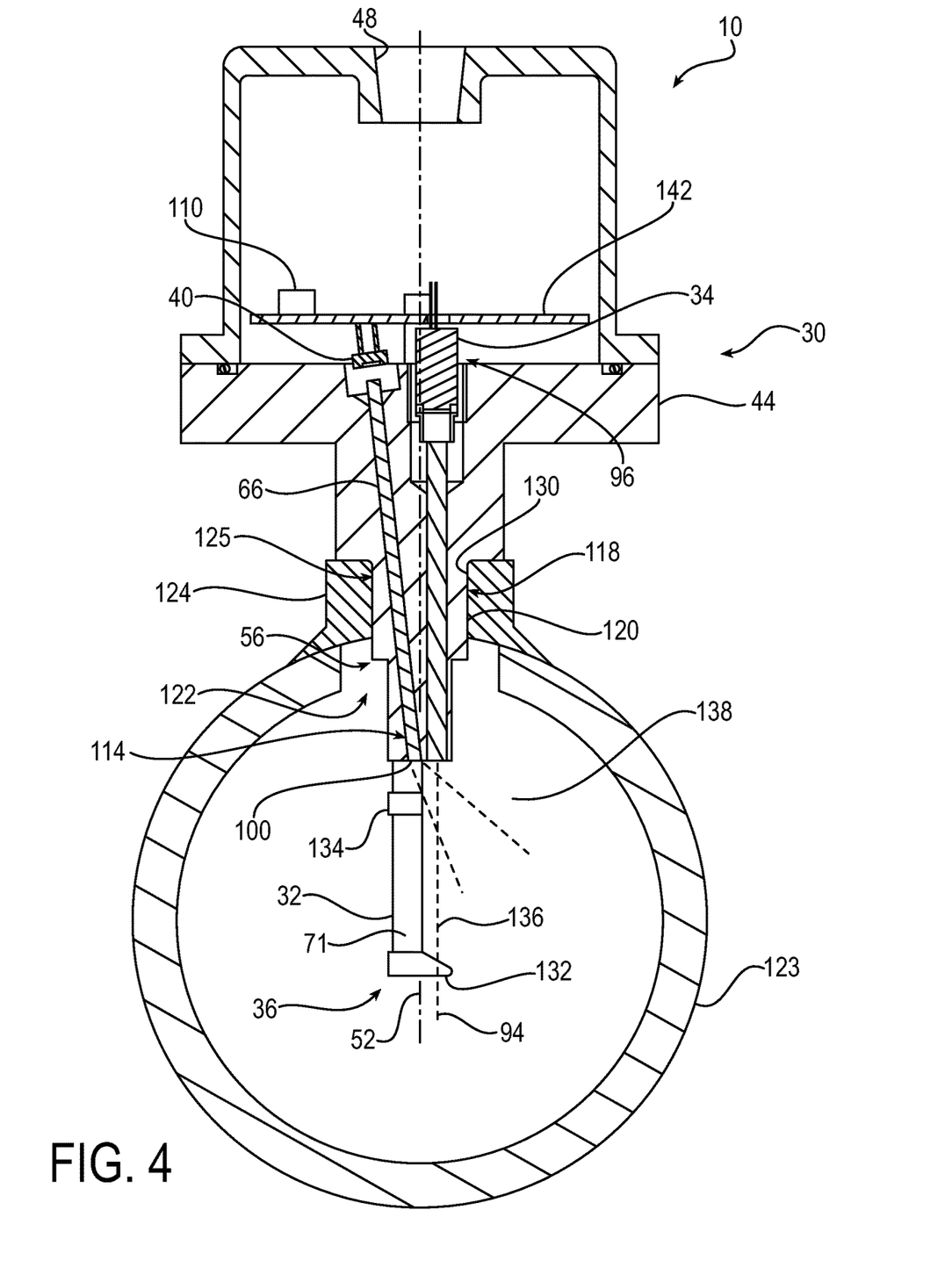
FIG. 4 is a cross-sectional view of the sensor system of FIG. 2, also taken along the line A-A of FIG. 2, and shown coupled to a fitting at a pipe section of a fluid system.

Turning now to FIG. 4, additional aspects of the sensor system 10 are detailed. A coupling section 118 of the main body portion 44 is disposed at the distal end 56 and adjacent the arm 32. The coupling section 118 includes threads 120 disposed proximally of the arm 32, allowing for securing of the sensor system 10 within an opening 122 in a pipe section 123 of a respective fluid system. The threads 120 extend fully circumferentially about the body axis 52, and are disposed proximally of the arm 32. Via the position of the threads 120 along the body axis 52, the sensor body 30 is configured to enable a full length of the arm 32, which is disposed distally of the threads 120, to be received into the opening 122 and into the respective fluid system.

The threads 120 and the coupling section 118 are sized to be received into an NPT fitting of the respective fluid system, such as into a standard quarter-inch NPT fitting 124 coupled to the pipe section 123 of the respective fluid system. The quarter-inch NPT fitting 124 defines a port 125 for receiving the sensor system 10. The quarter-inch NPT fitting 124 includes internal fitting threads 130 for engaging the external threads 120 of the coupling section 118. The sensor system 10 is able to be sized for receipt into the quarter-inch NPT fitting 124 in view of the longitudinal alignment of the light source receptacle 60 and light guide receptacle 64 parallel to one another.

In alternative embodiments, the threads 120 and coupling section 118 may be sized for receipt into a fitting of a different size, such as a standard three-quarter-inch NPT fitting. In some embodiments, the NPT fitting 124 may not be coupled to a pipe section and instead may be coupled to any other portion of a respective fluid system that allows for the arm 32 to be inserted into a fluid stream flowing through the respective fluid system.

Turning now to additional specific features of the arm 32 of the sensor system 10 shown in FIGS. 2-4, the arm 32 includes both a light absorbing beam dump 132 and a blocking member 134, each of which is positioned to restrict the light received at the inlet 100.

The beam dump 132 is disposed at the distal end 36 of the arm 32 and is positioned to be intersected by the projection axis 94 of the depicted laser light source 34. Thus, the laser light source 34 is aligned in the main body portion 44 to direct the laser beam, identified at 136 in FIG. 4, towards the beam dump 132. The beam dump 132 is configured to absorb at least a portion of light of the laser beam 136, such as via the material construction and/or color of the beam dump 132. The absorption aids in preventing at least a portion of light from the laser beam 136 from being reflected back towards the inlet 100 off of the distal end 36 of the arm 32. The beam dump 132 further protects the material of the pipe section 123 from being affected by the laser beam 136.

Intermediate the distal end 36/beam dump 132 and the distal end 56 of the main body portion 44, the blocking member 134, also herein referred to as a shadowing shelf 134, is positioned to block at least a portion of light from being received at the inlet 100. The shadowing shelf 134 extends transversely relative to the body axis 52, such as laterally between the adjacent arm portions 71 as illustrated in FIG. 2. The shadowing shelf 134 is positioned and sized to prevent intersection of the shadowing shelf 134 by the laser beam 136. In its orientation along the arm 32, the shadowing shelf 134 is positioned to block at least a portion of light from the laser beam 136 that is scattered and not absorbed by the beam dump 132 from being received at the inlet 100.

The shadowing shelf 134 is spaced from the distal end 114 of the fiber optic light guide 66 and is positioned to be intersected by the guide axis 112. In this way, as shown particularly in FIG. 4, the shadowing shelf 134 is positioned to restrict a field of intake 138 of light of the inlet 100 by blocking at least a portion of light from being received at the inlet 100.

Once light is received at the light sensor 40 via the inlet 100 and the fiber optic light guide 66, a processor 110 in the internal cavity 42, and operatively connected to the light sensor 40, analyzes an electrical output of the light sensor 40. The processor 110 is located at an electrical connection, such as a circuit board 142 that is retained in the internal cavity 42, such as via coupling to the main body portion 44. Each of the light sensor 40 and the laser light source 34 are connected to the processor 110 via the circuit board 142.

The processor 110 is configured to convert electrical signals from the light sensor 40 into digital data pertaining to one or more of intensity, consistency or quantity of the light received by the light sensor 40. For example, the processor 110 may include a control hardware component such as an application specific integrated circuit, a programmable logic device, a memory device containing instructions, or the like. The processor 110 is configured to calculate contaminant levels in the fluid stream corresponding to properties of the light received by the light sensor 40, such as in units of parts per million. The processor 110 also is configured to provide one or more of (i) an alarm indication, such as to an external device communicatively connected to the sensor system 10 when a contaminant threshold is reached, and (ii) an output signal to control a shutoff valve operatively connected to the sensor system 10 such as to prevent transfer of contaminated fluid downstream of the shutoff valve, and/or to provide a readable output of the level of contaminant such as at a display of an external device operatively connected to the sensor system 10.

The processor 110 may output data to an external device to allow for an audible or visual alarm, further data analysis, or data display via either of a wired or wireless transmission to the external device. To provide the transmission, a transmission element (not shown) may further be attached to the circuit board 142 or may be included in the processor 110, and thus operatively connected to the processor 110. A suitable transmission element may allow for wired or wireless connection of the sensor system 10 to an external processor of the external device, which as mentioned, may have a display operatively connected to the external processor. For example, when the processor 110 includes the transmission element, the processor 110 may be configured to transmit data converted from the light sensor 40 via the transmission element through any suitable network connection, such as cellular, WiFi, ethernet, Bluetooth, token ring, Zigbee, or the like.

The circuit board 142 also may provide for powering of the laser light source 34 and the light sensor 40. A power source (not shown) may be operatively connected to the circuit board 142 and located in the internal cavity 42. Alternatively, a power source may have a connection that extends through the passage 48 in the cap portion 46 to the circuit board 142, and thus may be located external to the sensor body 30. The processor 110, via the circuit board 142, controls power transmitted to the laser light source 34. For example, the processor 110 may control the laser light source 34 to continually emit a laser beam 136, or only to emit the laser beam 136 at predefined intervals.

In some embodiments, the laser light source 34 alternatively may be controlled by a control hardware component external to the sensor system 10, such as being connected to the circuit board 142 via a connection extending through the passage 48 in the cap portion 46. In other embodiments, the communication to an external control hardware component may be wireless.

In summary, a sensor system 10 for sensing contaminants within a fluid stream of a fluid system includes a sensor body 30 and an arm 32 extending from the sensor body 30 to a distal end 36 of the arm 32, a laser light source 34 configured to direct a laser beam 136 outwardly from an outlet of the sensor body 30, and a light sensor 40. A fiber optic light guide 66 is disposed in the sensor body 30 and extends from the light sensor 40 to an inlet 100 of the sensor body 30 for directing light to the light sensor 40. A beam dump 132 is positioned at the distal end 36 opposite the laser light source 34 to absorb at least a portion of the laser beam 136 directed towards the distal end 36. A blocking member 134 of the arm 32 is disposed intermediate the sensor body 30 and the distal end 36 and is configured to partially restrict a field of intake 138 of light at the inlet 100.

In use, the sensor system 10 is oriented in a pipe section 123 of a respective fluid system via the threads 120, such that the field of intake 138 is oriented directly in a fluid stream flowing through the pipe section 123. More particularly, the sensor system 10 is shaped to orient the field of intake 138 spaced radially inwardly from internal walls of the respective pipe section 123. In this way, interaction may be had with a portion of the respective fluid stream generally centrally-located within the respective pipe section 123 that is representative of the fluid make-up and is affected less by flow effects or anomalies adjacent internal pipe walls of the pipe section 123. The sensor system 10, also via the threads 120, is configured for insertion into a pipe section using a standard quarter-inch NPT fitting. No cutting of pipe sections or specially designed fittings are necessary to couple the sensor system 10 via an alternatively sized fitting.

When the sensor system 10 is inserted into a fluid stream and the depicted laser light source 34 is activated by the processor 110, the laser beam 136 is emitted from the illustrated laser light source 34 towards the beam dump 132 and the distal end 36 of the arm 32. The changes in the light from the laser beam 136, and the light reflected off water contaminant in the fuel, are received at the inlet 100, and transmitted along the depicted fiber optic light guide 166 to the light sensor 40. The combination of the depicted laser light source 34 and the fiber optic light guide 166 provides for a stable and less sensitive sensor system with respect to optical changes and measurement shift typically experienced in conventional systems.

The electrical signals output from the sensor 40 are converted and analyzed, thus converting the electrical signals into output relating to consistency, quantity, and intensity of light analyzed, and into determinations of the level of contaminant in the fuel, such as in units of parts per million. As mentioned, the processor 110 may be configured to provide an alarm indication when a contaminant threshold is reached, to control a shutoff valve operatively connected to the sensor system 10, and/or to provide a readable output of the level of contaminant, such as at a display operatively connected to the sensor system 10.

The present invention also provides a method of sensing contaminants within a fluid stream. The method includes (a) emitting a laser beam 136 from a laser light source 34 into the fluid stream that may include a contaminant, (b) receiving light from the laser beam 136 reflected from the fluid stream at a fiber optic light guide 66, and (c) transmitting the light along the fiber optic light guide 66 to a light sensor 40. The method also includes (d) analyzing one or more properties of the light, such as intensity or consistency, and (e) determining the level of contaminant in view of the one or more properties, such as based on changes in intensity or consistency of the light transmitted to the light sensor 40. The method also may include partially absorbing light of the laser beam 136 to prevent the absorbed portion of the laser beam 136 from being reflected back towards the inlet 100, such as through use of a beam dump 132. The method further may include partially blocking light from being received at the fiber optic light guide 166 with a blocking member 134 spaced from a distal end 114 of the fiber optic light guide 66 opposite the light sensor 40.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A sensor system for sensing contaminants within a fluid stream, the sensor system comprising:
 a sensor body and an arm extending from the sensor body to a distal end of the arm, wherein the arm is insertable into the fluid stream;
 a light source disposed in the sensor body and configured to direct a light beam outwardly from an outlet of the sensor body towards the distal end of the arm;
 a light sensor disposed in the sensor body and the sensor body having an inlet disposed opposite the light sensor, the inlet being positioned to receive and direct light towards the light sensor; and
 a beam dump positioned at the distal end of the arm opposite the light source to absorb at least a portion of the light beam directed towards the distal end of the arm, thereby preventing the absorbed portion of the light beam from being reflected back towards the inlet;
 wherein the arm includes a shelf that is disposed intermediate between the sensor body and the distal end of the arm, the shelf being configured to partially restrict a field of intake of light at the inlet.

2. The sensor system of claim 1, wherein the shelf extends transversely relative to a longitudinal axis of the arm along which the arm extends.

3. The sensor system of claim 1, wherein the shelf is positioned to block at least a portion of light scattered and not absorbed by the beam dump from being received at the inlet.

4. The sensor system of claim 1, wherein the arm includes a passage through the arm for allowing flow of the fluid stream therethrough to minimize effect of the arm on fluid stream.

5. The sensor system of claim 1, wherein the sensor body includes external threads for securing the sensor system within an opening in a fluid system, and wherein the sensor system at the external threads is sized to be received into a quarter-inch NPT fitting.

6. The sensor system of claim 1, in combination with a fluid system having a quarter-inch NPT fitting defining a port for securely receiving the sensor system therein, the sensor body having external threads sized to be received into the quarter-inch NPT fitting, and the fitting having corresponding fitting threads for engaging the external threads.

7. The sensor system of claim 1, further comprising a light guide disposed in the sensor body and extending from the light sensor to a distal end of the light guide opposite the light sensor at the inlet of the sensor body, wherein the light guide is aligned for directing light through the sensor body to the light sensor to enable receipt of the light by the light sensor.

8. The sensor system of claim 7, wherein the light guide is a fiber optic light guide.

9. The sensor system of claim 7, wherein the light guide extends along a guide axis that is transverse a projection axis of the light beam extending from the light source to the outlet of the sensor body.

10. The sensor system of claim 7, wherein the light guide extends along a guide axis and wherein the shelf is positioned to be intersected by the guide axis.

11. The sensor system of claim 1, wherein the inlet of the sensor body is disposed adjacent the outlet of the sensor body.

12. The sensor system of claim 1, further including a processor disposed in the sensor body and configured to convert electrical signals from the light sensor into digital data pertaining to one or both of intensity or consistency of the light received by the light sensor.

13. The sensor system of claim 1, further including a processor operatively connected to the light source and to the light sensor for powering the light source and the light sensor, and for calculating contaminant levels in the fluid stream corresponding to properties of the light received by the light sensor.

* * * * *